United States Patent [19]

Wada et al.

[11] Patent Number: 4,636,849

[45] Date of Patent: Jan. 13, 1987

[54] APPARATUS FOR INSPECTING SOLID DRUGS AND A METHOD THEREFOR

[75] Inventors: Yasutaro Wada, Suita; Takashi Ohtsuki, Kawabe, both of Japan

[73] Assignee: Takeda Chemical Industries, Ltd., Osaka, Japan

[21] Appl. No.: 672,388

[22] Filed: Nov. 16, 1984

[30] Foreign Application Priority Data

Nov. 26, 1983 [JP] Japan ............................ 58-222711

[51] Int. Cl.⁴ .......................................... H04N 7/18
[52] U.S. Cl. ...................................... 358/106; 358/101
[58] Field of Search ..................... 358/101, 106, 96; 250/562, 563, 223 B; 356/237, 240

[56] References Cited

U.S. PATENT DOCUMENTS

| | | | |
|---|---|---|---|
| 3,560,096 | 2/1971 | Watson et al. | 358/101 X |
| 3,775,556 | 11/1973 | Nagamatsu | 358/106 |
| 4,349,739 | 9/1982 | Annis | 358/106 X |
| 4,446,481 | 5/1984 | Edamatsu et al. | 358/106 |
| 4,486,777 | 12/1984 | Yamamura | 358/106 |

Primary Examiner—Howard W. Britton
Assistant Examiner—Victor R. Kostak

Attorney, Agent, or Firm—Wenderoth, Lind & Ponack

[57] ABSTRACT

An apparatus for detecting the presence of a foreign matter on each solid drug item by scanning the surface of the solid drug item with a television camera and for generating a pulse signal when the level of a scanning signal thereof exceeds a predetermined value includes a shift register for temporarily storing, for each address, the pulse signal per scan line of the camera and for outputting the signal sequentially for each address during the next succeeding scan; an OR gate for receiving both an address output from the shift register and the next succeeding address output; an AND gate for receiving both an output from the OR gate and an output at the address corresponding to the address output at the next succeeding scan line; a counter for counting pulse signals fed thereto from the AND gate; and an output circuit for generating a detection signal indicative of the detection of foreign matter when the count of the counter is greater than a predetermined value, whereby a pulse signal bridging between the neighboring addresses and also between the adjoining scan lines can be output by the counter so that foreign matter of a length and width corresponding to the output thereof can be detected.

2 Claims, 11 Drawing Figures

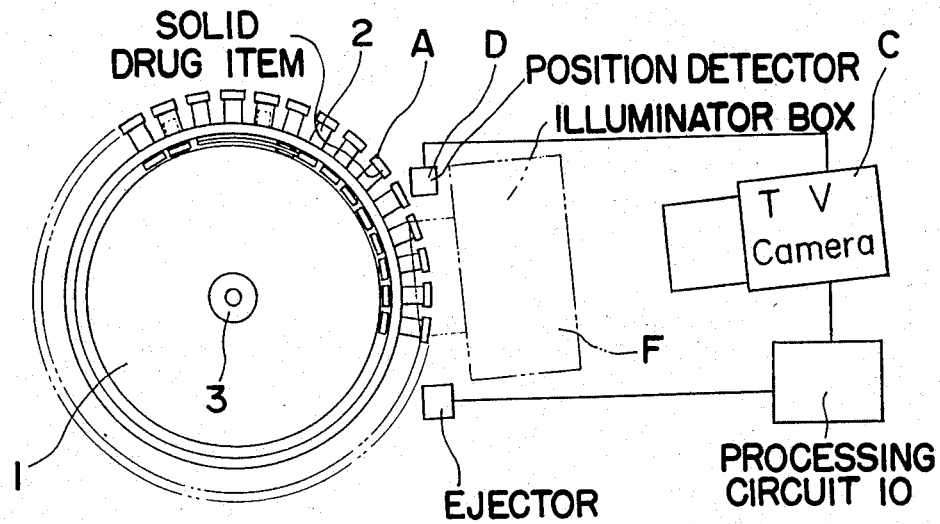
Fig. 1
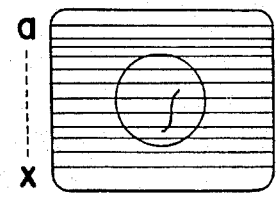
Fig. 4(a)
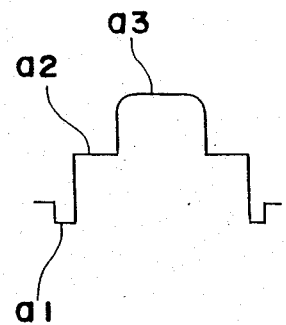
Fig. 4(b)
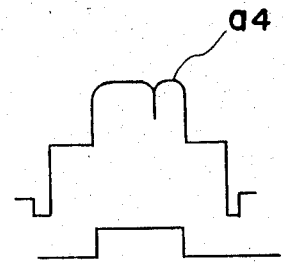
Fig. 4(c)
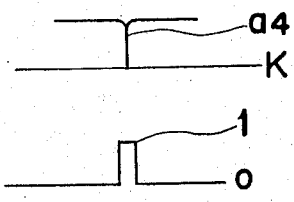
Fig. 4(d)
Fig. 4(e)
Fig. 4(f)

APPARATUS FOR INSPECTING SOLID DRUGS AND A METHOD THEREFOR

BACKGROUND OF THE INVENTION

The present invention relates to an apparatus and a method for inspecting solid drugs for the detection of the presence of foreign matter on the solid drugs by scanning the surface of each solid drug item by the use of a television camera and generating a pulse signal when the level of a video scanning signal thereof exceeds a predetermined value.

More specifically, the present invention relates to the inspection of the surface of each solid drug item by inspecting the pulse signal bridging between the neighboring addresses in each scan line of the television camera and/or between the neighboring scan lines of the television camera and detecting the presence of foreign matter of a length and width corresponding to an output thereof.

Solid drugs such as tablets and pills are usually a compacted pharmaceutical preparation containing one or more powdery medicaments. It is often found that some of the solid drug items have indentations on the surface because of the containment of particles and some of them have attached thereto fibrous foreign matter originally included in one or more constituent medicaments and/or fibrous foreign matter such as hairs and/or textile fibers floating in the air.

As is well known to those skilled in the art, medicines should in no way contain foreign matter contained therein or adhering thereto and, even though they are prepared and manufactured under a controlled atmosphere, no complete elimination of the possibility of foreign matter adhering to and/or contained in the solid drugs can be possible. Specifically, of foreign matter, hairs are that which purchasers and patients dislike most and which often constitute a major cause of the blackened reputation of the manufacturer. Since the manufacture of medicine requires the intervention of many people, the inclusion and/or adherence of hairs can not be completely eliminated. The hairs tending to adhere to, or to be contained in, medicine are very fine in most cases, and therefore, it has long been desired to detect the presence of hairs, so fine as to be smaller than 100 micrometers, in the solid drugs by the use of an inspecting machine and, then, to eject the solid drug items, found to have the hairs, from the production line. It is pointed out that even hairs of about 50 micrometers in thickness are noticeable because they have length.

Hitherto, those solid drug items having such foreign matter have been removed from the inspection line as defective products. The inspection and the removal are carried out by the intervention of human labor, specifically the naked eyes and hands of one or more inspectors, and therefore, such problems as associated with errors in inspection and/or the departure from the inspection standards can hardly be avoided. This in turn results in the fact that the solid drugs often fail to satisfy the requirements concerning the surface precision to such an extent as to bring about the unpleasant sensation to those who are administered such solid drugs. In view of this, the automation of the inspection line has long been expected.

SUMMARY OF THE INVENTION

In an electric circuit capable of generating a pulse signal when the level of a video signal obtained by scanning the surface of a solid drug with a television camera exceeds a predetermined value, when the sensitivity is increased to a value higher than that of the conventional discriminator, it can generate the pulse signal in response to the detection of a piece of foreign matter of about 50 micrometers in size. On the other hand, with regard to the video signal of a good product, it is a general practice to output the pulse signal at a certain rate in response to the detection of indentations and/or very fine foreign matter on the surface of the solid drug.

The present invention has been developed with a view aimed at the fact that, while the pulse signal representative of the presence of fibrous foreign matter such as hairs is generated in the form of a train of pulses since fibrous foreign matter has length, the pulse signal representative of a good product is generally generated at random so that, by utilizing a temporary storage circuit of a shift register, the inspection of the presence of fine fibrous foreign matter such as hairs can be achieved.

Accordingly, the present invention has for its essential object to provide an apparatus, and also a method, for automatically sorting from other solid drug items only the solid drug items which have on their surface fibrous foreign matter of a length and a width exceeding, for example, 50 microns, in view of the finding that the surface indentations of the solid drugs resulting from the containment of particles of one or more constituent medicaments are of a size smaller than 50 microns whereas fibrous foreign matter on the surface of the solid drugs resulting from the inclusion of hairs or the like are of a size exceeding $50 \times 500$ microns.

To this end, a method according to the present invention for detecting fibrous foreign matter of a size greater than a predetermined size appearing on the surface of any one of the solid drug items comprises scanning the surface of the respective solid drug item by the use of a television camera, generating a pulse signal indicative of the detection of foreign matter after the discrimination of a signal on the scan line which is greater than a predetermined level, counting the number of scan lines which are contiguous to each other at the time said pulse signal has generated at address locations adjoining each other in correspondence to the neighboring scan lines, and determining foreign matter only when the count of the number of the scan lines is greater than a predetermined value.

It is to be noted that the counting of the number of the scan lines referred to above may be carried out by the use of either a comparing counter or a combination of an AND circuit and a presetting switch.

The apparatus according to the present invention for detecting the presence of foreign matter on solid drugs by scanning the surface of each solid drug item with the use of the television camera and generating a pulse signal when the level of the video signal thereof exceeds a predetermined value comprises: a shift register for temporarily storing, for each address, the pulse signal per scan line of the television camera and for outputing the pulse signal sequentially for each address during the next succeeding scan; an OR means for receiving both an address output from the shift register and the next succeeding address output; an AND means for receiving both an output from the OR means and an output at the address corresponding to said address output at the next succeeding scan line; a counting means for counting pulse signals of an output from the AND means; and a means for generating a detection signal indicative of the detection of foreign matter when the count of the counting means is greater than a predetermined value, whereby a pulse signal bridging between the neighboring addresses and also between the adjoining scan lines can be taken out by the counting means so that foreign matter of a length and a width corresponding to the output thereof can be detected.

BRIEF DESCRIPTION OF THE DRAWINGS

This and other objects and features of the present invention will become clear from the following description taken in conjunction with preferred embodiments thereof with reference to the accompanying drawings, in which:

FIG. 1 is a schematic front elevational view showing a solid drug inspecting machine according to one embodiment of the present invention;

FIGS. 4(a) to 4(f) are diagrams showing waveforms of various signals appearing in the circuit of FIG. 2;

DETAILED DESCRIPTION OF THE EMBODIMENTS

Figure 2:
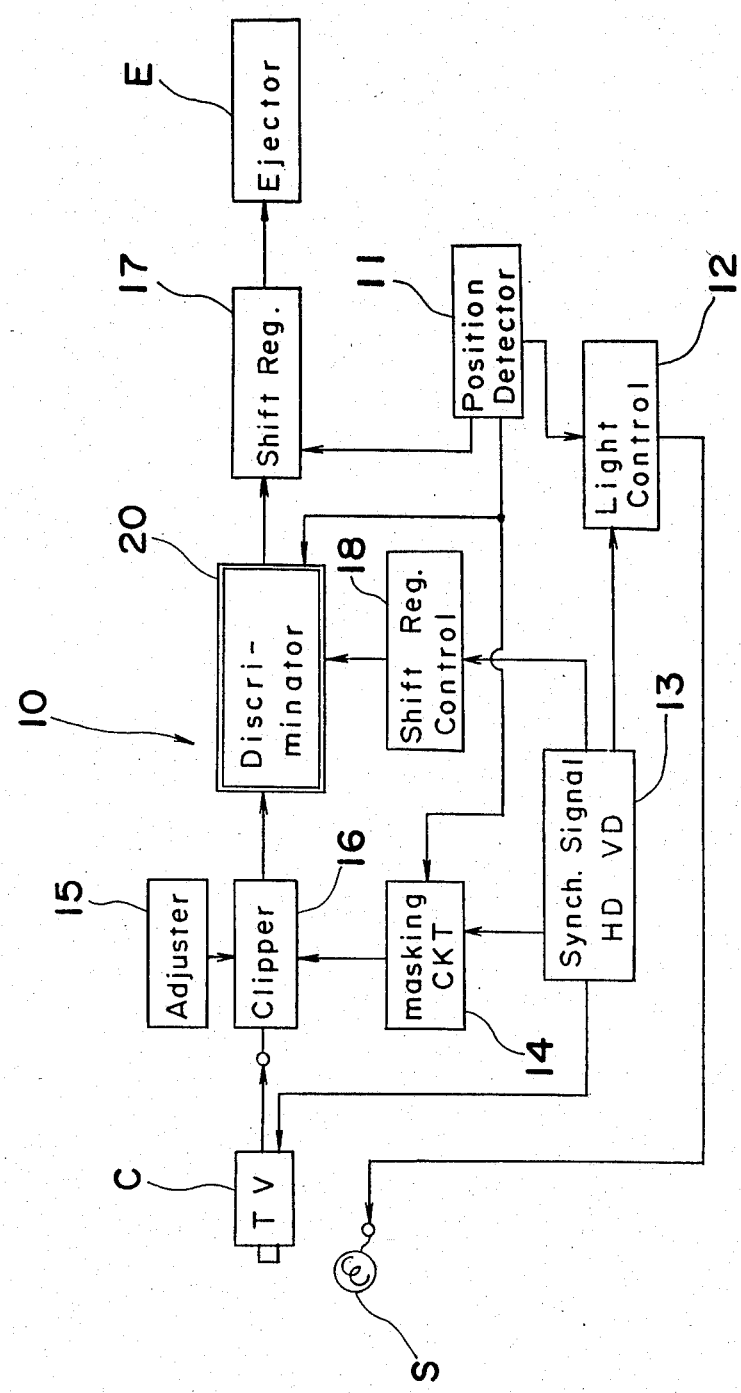
FIG. 2 is a circuit block diagram showing the detail of a processing circuit shown in FIG. 1.

Before the description of the present invention proceeds, it is to be noted that like parts are designated by like reference numerals throughout the accompanying drawings.

Referring first to FIG. 1, a solid drug inspecting machine according to the present invention comprises: a drug transport system including a generally plate-like supply drum 1 having a plurality of circumferentially equally spaced and radially outwardly protruding receptacles 2; a means (not shown) for driving a drive shaft 3 to rotate the drum 1 in one direction together therewith; a means (not shown) for communicating some of the receptacles 2 to a source of a vacuum so as to permit the solid drug items to be carried thereby during the rotation of the drum 1 past an inspecting station; a means (not shown) for communicating some of the receptacles 2 to a source of compressed air so as to permit the solid drug items, which have been successively moved past the inspecting station while carried by said some of the receptacles 2, to be released from said some of the receptacles 2 when the drum 1 has been rotated past the inspecting station; an inspecting system including a television camera C installed at the inspecting station adjacent the drum 1, a processing circuit 10 for processing video scan signals from the television camera C, an illuminator box F positioned frontwardly of the television camera C, and a peripheral system including a position detector D positioned at a predetermined location adjacent the drum 1 for detecting the position of each solid drug item A to be inspected; a means (not shown) for feeding the solid drug items onto the receptacles 2 one at a time; a means (not shown) for receiving the solid drug items A released successively from the respective receptacles 2, an ejector E (not shown) for ejecting from the receptacles 2 the solid drug items which have been detected to be defective products. The inspecting machine of the construction described above is so designed that, while the solid drug items A supplied by the supplying means onto the supply drum 1 are sucked in and received by the respective outer open ends of the receptacles 2, they can be moved past the inspecting station as the drum 1 is rotated by the drive means in one direction about the drive shaft 3 so that they can be scanned by the television camera C operatively associated with the position detector D to produce a video signal which is subsequently processed by the processing circuit 10 wherefor, when the solid drug item is determined as having an abnormality on the surface thereof, the ejector means E is activated to remove the solid drug item from the drum 1 separately of the receiving means.

A video signal of the solid drug item A viewed by the television camera is taken out in the form of a video scan signal having a plurality of scan lines a . . . x as shown in FIG. 4(a), each of said scan lines being, as shown in FIG. 4(b), comprised of a synchronizing signal a1, a reference level a2 and a video signal a3. Where the solid drug item A viewed by the television camera contains at least one piece of foreign matter, such as hairs, indentations and stresses, the video signal will be found to have a defect detection area a4 at which its level drops as shown in FIG. 4(c).

FIG. 2 illustrates a block diagram of the processing circuit 10 for processing the video signal output from the television camera C, which includes a position detector 11 for receiving a position signal from the means comprised of, for example, an encoder for detecting the position of the solid drug item A to be inspected; an output from said position detector 11 is utilized to drive a light control 12 for a strobe lamp S for illuminating the solid drug item A. The television camera C for viewing the solid drug item A to be inspected is activated by an output from a horizontal and vertical synchronizing signal circuit 13. The video signal from the television camera C is identified as to a region of each scan line to be inspected, that is, the total number of the addresses of the scan line, as shown in FIG. 4(d), by an inspecting mask circuit 14 operable in synchronism with an output from the position detector 11 for determining an area of the solid drug item to be inspected. At the same time, the defect detect portion of the region of each scan line to be inspected, having a level lower than a predetermined level K, is detected by a clipper circuit 16 in response to an output from a level sensitivity adjuster 15 for determining the level sensitivity of the defect detect portion. The clipper circuit 16 generates a high level signal "1" (as shown in FIG. 4(f)), in the event that the scan line contains the defect detect portion as shown in FIG. 4(e), or a low level signal "0" in the event that the scan line contains no defect detect portion, for each address of the scan line in a manner as tabulated in Table 1.

TABLE 1

| Scan Line No. | Scan Line Address (n addresses) | | | | | | | | | | | | |
|---|---|---|---|---|---|---|---|---|---|---|---|---|---|
| | n | — | — | — | — | — | — | — | — | — | 4 | 3 | 2 | 1 |
| #1 | 0 | — | — | — | — | — | — | — | — | — | 0 | 0 | 1 | 0 |
| #2 | 0 | — | — | — | — | — | — | — | — | — | 0 | 1 | 1 | 0 |
| #3 | 0 | — | — | — | — | — | — | — | — | — | 0 | 0 | 1 | 1 |
| — | — | — | — | — | — | — | — | — | — | — | — | — | — | — |
| — | — | — | — | — | — | — | — | — | — | — | — | — | — | — |

Figure 3:
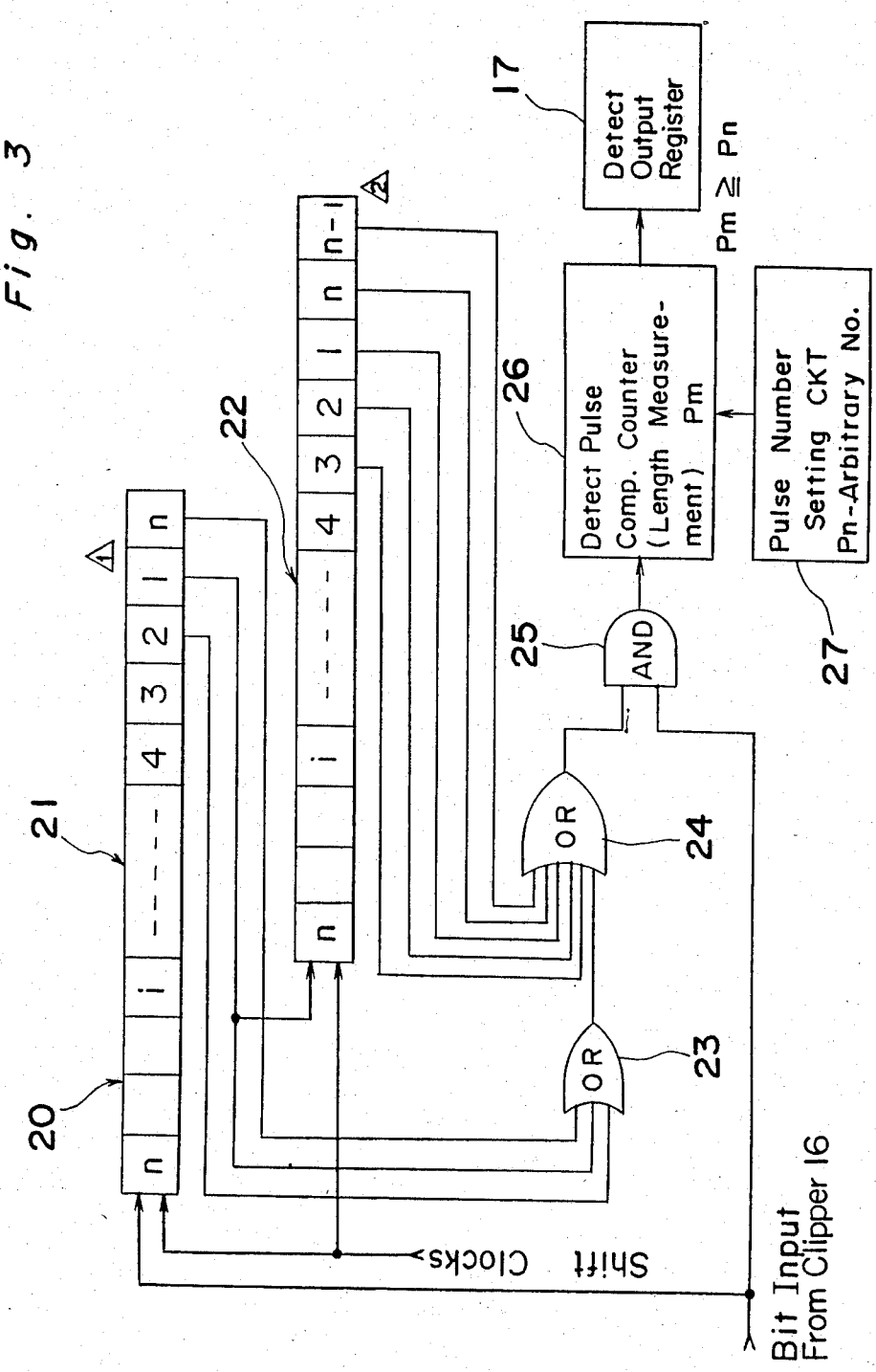
FIG. 3 is a circuit block diagram showing the details of a discriminator used in the circuit of FIG. 2.

The output from the clipper circuit 16 generated in the manner as tabulated in Table 1 is fed to a discriminator 20 operable in synchronism with the output from the position detector 11. As shown in FIG. 3, this discriminator 20 comprises a first shift register 21 and an AND gate 25 to which the binary output from the clipper circuit 16 is fed, a second shift register 22 connected in series with the first shift register 21, a first OR gate 23 for receiving three address signals (signals from the addresses n, 1 and 2) from the first shift register 21, a second OR gate 24 for receiving an output from the first OR gate 23 and five address signals (signals from the addresses n−1, n, 1, 2 and 3) from the second shift register 22, a counter 26 for counting the number of pulses output from the AND gate 25 which receives both the output from the clipper circuit 16 and the output from the second OR gate 24, and a setting circuit 27 for setting the preset number of pulses for the counter 26. The signal generated when the counter 26 has counted a number of pulses which is greater than the preset number of pulses determined by the setting circuit 27 is inputted to a shift register 17 for the defect detect signal which operates in synchronism with the output from the position detector 11 to generate an output signal used to operate an ejector E for ejecting the defective solid drug item. It is to be noted that, in practice, n equals 325, the power of resolution is about 100 micrometers and the shift register is comprised of three MC1456Z (Motorola) and two MC14015 (Motorola).

Each of the first and second shift registers 21 and 22 in the discriminator 20 has a plurality of bits corresponding in number to the total number of the addresses of the respective scan lines and is operable, upon receipt of a clock signal fed thereto from the synchronizing signal circuit 13 through a shift register control 18, to sequentially shift bit by bit the binary signal which has been fed from the clipper circuit 16 for each address of the scan line, the binary output from the first shift register 21 being sequentially fed bit by bit to the second shift register 22. For this reason, for example, as shown in Table 1, the n-bit of the second shift register 22 is inputted with, as the address signal of each scan line, the binary signal representative of the address n number in a first scan line and, at the same time, the n-bit of the first shift register is inputted with the binary signal representative of the address n number in a second scan line as shown in Table 2. When the binary signal representative of a first address in a third scan line is inputted to an n-th bit of the first shift register 21 from the clipper circuit 16, and when the binary signal in each bit of the first shift register 21 is shifted bit by bit, the binary signal in a first bit of the first shift register 21 is inputed to an n-th bit of the second shift register 22, and the binary signal in each bit of the second shift register 22 is sequentially shifted bit by bit while the binary signal in the first bit of the second shift register 22 diminishes.

TABLE 3

|  | First OR Gate | Second OR Gate | AND Gate |
|---|---|---|---|
| Input 1 | 0, 0, 1 → | →1, 0, 0, 0, 0, 1 | 1, 1 |
| Output 1 | 1 → | 1 | 1 |
| Input 2 | 1, 0, 0 → | →1, 0, 0, 0, 0, 0 | 1, 1 |
| Output 2 | 1 → | 1 | 1 |
| Input 3 | 0, 0, 0 → | →0, 0, 1, 0, 1, 0 | 1, 1 |
| Output 3 | 0 → | 1 | 1 |

At this time, as shown in Table 3, the first OR gate 23 generates a high level signal "1" only when one of the binary signals in the first to third bits of the first shift register 21, that is, one of the binary signals at the n-th, first and second addresses of the second scan line, is in a high level state, which high level signal is then applied to the second OR gate 24. When one of the binary signals in the first to fifth bits of the second shift register 22, that is, the binary signals at the n−1th, n-th, and first to third addresses of the first scan line, and the output from the first OR gate 23 is in a high level state, the second OR gate 24 generates a high level signal "1" which is in turn fed to the AND gate 25. Accordingly, the AND gate 25 generates a high level signal "1", when both the binary signal at the first address of the third scan line and the output from the second OR gate 24 are in a high level state "1". This high level signal "1" from the AND gate 25 is in turn fed to the counter 26 whereat the number of the high level signals fed from the AND gate 25 is counted. In the event that the count given by the counter 26 exceeds the preset number determined by the setting circuit 27, a detection signal indicative of the detection of a defect is outputed from the counter 26 to the shift register 17. When the binary signal of the second address in the third scan line is subsequently fed from the clipper circuit 16 to both the n-th bit of the first shift register 21 and the AND gate, the above described process takes place sequentially in a manner described above. Therefore, by temporarily storing the pulse signal for each scan line of the camera C in the shift registers 21 and 22 for each address, then outputting sequentially for each address during the subsequent scanning, taking out, by the use of the gates 23, 24 and 25, the pulse signal which bridges the adjacent three addresses and the succeeding three scan lines, and taking out the consecutive output from the counter 26, it is possible to eject or remove foreign matter of a predetermined width and length by the use of the ejector E.

Figure 5:
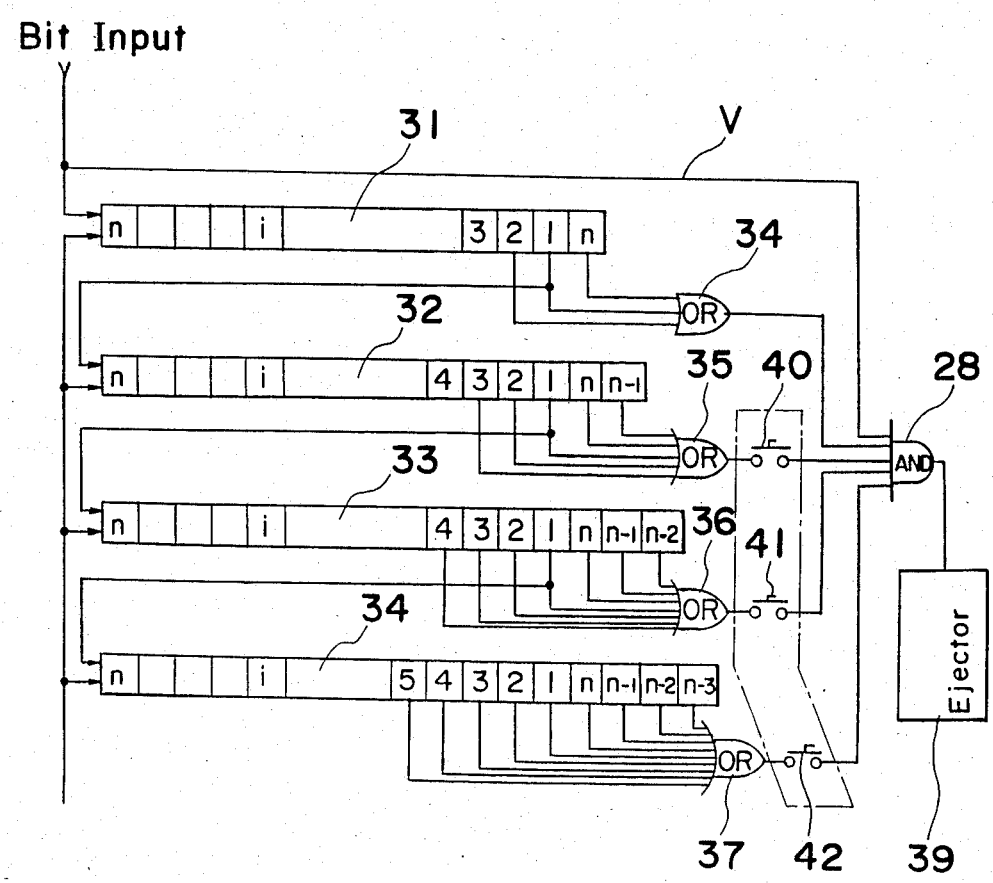
FIG. 5 is a diagram similar to FIG. 3, showing a modified form of the discriminator.

The discriminator 20, the details of which have been described with reference to and shown in FIG. 3, may be constructed as shown in FIG. 5 according to another preferred embodiment of the present invention. In the preferred embodiment, the number n of the addresses per horizontal scan of a shift register is 325, and the field of view of the television camera is about 36 mm in the horizontal direction and about 26 mm in the vertical direction. Accordingly, the power of resolution in the horizontal direction is 110 micrometers, and that in the

TABLE 2

|  | First Shift Reg. (n bits) |  |  |  |  |  |  | Second Shift Reg. (n + 2 bits) |  |  |  |  |  |  |  |
|---|---|---|---|---|---|---|---|---|---|---|---|---|---|---|---|---|
|  | n | n−1 | 5 | 4 | 3 | 2 | 1 | n | n−1 | 5 | 4 | 3 | 2 | 1 | n | n−1 |
| input 1 | 0 | 0 | 1 | 0 | 0 | 0 | 0 | 1 | 0 | 0 | 1 | 0 | 0 | 0 | 0 | 1 |
| input 2 | 0 | 0 | 0 | 0 | 1 | 1 | 0 | 0 | 0 | 0 | 1 | 0 | 0 | 0 | 0 | 0 |
| input 3 | 1 | 0 | 1 | 0 | 0 | 0 | 0 | 0 | 1 | 0 | 0 | 0 | 1 | 0 | 1 | 0 | vertical direction is 106 micrometers because, according to the camera involved in the present embodiment, there are 244 lines aligned in the vertical direction. Thus, the aspect ratio is 1:1. FIG. 5 illustrates a method wherein no counter for the length measurement such as used in the embodiment of FIG. 3 is used and, instead, setting switches 40, 41 and 42 are used for the length measurement. The discriminator shown in FIG. 5 comprises four shift registers 31, 32, 33 and 34, four OR gates 34, 35, 36 and 37, an AND gate 28, three setting switches 40, 41 and 42 which may each be a dip switch and ejector 39.

If the fibrous foreign matter viewed by the television camera lies generally vertically relative to the horizontal scan line, the image of the foreign matter is horizontally scanned five times and, at the time a pulse signal thereof appears on a binary input line V, the defective pulse signal already scanned is stored in a first address of each of the shift registers. On the other hand, where the fibrous foreign matter viewed by the television camera lies at an angle of 45° relative to the horizontal scan line, the address of the defective pulse signal in each shift register has an inclination of 45°, that is, the defective pulse signal is stored at the address 2 or n in the first shift register 31, at the address 3 or n−1 in the second shift register 32, at the address 4 or n−2 in the third shift register 33 and at the address 5 or n−3 in the fourth shift register 34.

Figure 6:
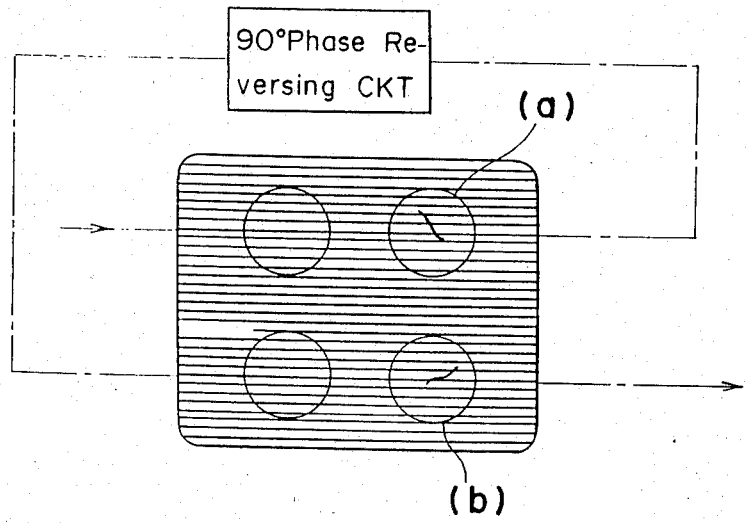
FIG. 6 is a schematic representation showing the method wherein four solid drug items are simultaneously scanned by a common television camera.

Accordingly, with the discriminator 20 constructed as shown in FIG. 5, where the fibrous foreign matter lies at an angle smaller than 45° relative to the horizontal scan line, it will deviate from the address of each shift register which provides an input to the associated OR gate and, therefore, no detection signal can be generated. In order for the detection signal to be generated even when the angle of inclination of the foreign matter relative to the horizontal scan line is smaller than 45°, two possibilities can be contemplated. One is to increase the number of addresses of each shift register which provides an input to the associated OR gate. Since the unnecessary increase of the addresses brings no corresponding increase in efficiency, the problem is solved by another method which will now be described. In the preferred embodiment, four solid drug items are simultaneously viewed by the television camera as shown in FIG. 6. While the solid drug items being inspected are, when viewed on a television monitor screen, moving from top to bottom (or from bottom to top), they are cast in the form of still images because of the illumination by the strobe lamps.

The inspection of the solid drug items is carried out at a speed of 30 times per second, and the solid drug items are transported at a rate of 30 pitches per second. Therefore, in FIG. 6, the solid drug items are inspected two times at upper and lower positions. On the other hand, since each solid drug item is retained by a respective suction nozzle rotatable about its own longitudinal axis, and since it can be turned 90° during the movement over one pitch from (a) towards (b) in FIG. 6, the angle of inclination will be within 45° relative to the vertical and the solid drug can be inspected in all directions, thereby solving the above described problem.

From the foregoing full description of the present invention, it has now become clear that the apparatus as well as the method according to the present invention are effective to precisely and automatically examine the solid drug items and to increase the yield of production.

Although the present invention has fully been described in connection with the preferred embodiments thereof with reference to the accompanying drawings, it is to be noted that various changes and modifications are apparent to those skilled in the art. By way of example, since the length of the foreign matter, that is, the number of scan lines, varies with the magnification factor at which it is viewed by the television camera, a counting comparator may be so designed that the preset value can be adjustable to suit the length desired to be detected.

Therefore, such changes and modifications are to be construed as included within the true scope of the present invention as defined by the appended claims, unless they depart therefrom.

What is claimed is:

1. An apparatus for detecting the presence of foreign matter of a plurality of solid drug items by scanning a surface of each solid drug item with a television camera and generating a pulse signal when a level of a video signal output from said camera exceeds a predetermined value, said apparatus comprising: a shift register for temporarily storing a pulse signal generated for each respective address of a scan line of said television camera and for sequentially outputting said stored pulse signal during a next scan; an OR means for receiving both an output from said shift register at a particular address and an output thereof at a next address adjacent said particular address; an AND means for receiving both an output from said OR means and an output from said shift register at an address corresponding to said particular address but at a next scan line scanned by said camera; a counting means for counting pulse signals which are output from said AND means, and a means for generating a detection signal indicative of the detection of foreign matter when said counting means has counted up a number of pulse signals which is greater than a predetermined value, whereby a pulse signal corresponding to adjacent addresses along one scan line and also between the same addresses of two adjacent scan lines are counted by said counting means so that foreign matter of a length and width corresponding to the output thereof can be detected.

2. A method for detecting foreign matter of a size greater than a predetermined size appearing on a surface of a solid drug comprising the steps of: scanning the surface of the solid drug with a television camera; generating a pulse signal indicative of the detection of foreign matter after a determination that a video signal of a scan line output of the television camera is greater than a predetermined level; counting the number of the scan lines which are contiguous to each other and which a pulse signal has been generated at identical address locations in adjacent scan lines, and determining that foreign matter is present only when the counted number of scan lines is greater than the predetermined value.

* * * * *